United States Patent [19]
McCue

[11] Patent Number: 5,788,701
[45] Date of Patent: Aug. 4, 1998

[54] INSTRUMENT SYSTEM FOR KNEE PROTHESIS IMPLANTATION WITH UNIVERSAL HANDLE OR SLAP HAMMER

[75] Inventor: Diana F. McCue, Pocasset, Mass.

[73] Assignee: Johnson & Johnson Professional, Inc., Raynham, Mass.

[21] Appl. No.: 843,551

[22] Filed: Apr. 18, 1997

Related U.S. Application Data

[63] Continuation of Ser. No. 576,744, Dec. 21, 1995, abandoned.

[51] Int. Cl.[6] .................................................. A61B 17/56
[52] U.S. Cl. .............................. 606/88; 606/86; 606/99; 623/20
[58] Field of Search ............................ 606/86, 87, 88, 606/89, 99, 100, 53; 623/20

[56] References Cited

U.S. PATENT DOCUMENTS

| | | | |
|---|---|---|---|
| 3,036,482 | 5/1962 | Kenworthy et al. | 173/90 |
| 4,459,985 | 7/1984 | McKay et al. | 128/303 R |
| 4,587,964 | 5/1986 | Walker et al. | 606/85 |
| 4,765,328 | 8/1988 | Keller et al. | 606/85 |
| 4,921,493 | 5/1990 | Webb, Jr. et al. | 606/85 |
| 5,037,423 | 8/1991 | Kenna | 606/88 |
| 5,122,144 | 6/1992 | Bert et al. | 606/88 |
| 5,443,471 | 8/1995 | Swajger | 606/99 |
| 5,499,984 | 3/1996 | Steiner et al. | 606/80 |
| 5,499,985 | 3/1996 | Hein et al. | 606/99 |
| 5,499,986 | 3/1996 | Dimarco | 606/104 |

FOREIGN PATENT DOCUMENTS

| | | |
|---|---|---|
| 0 474 320 A1 | 11/1992 | European Pat. Off. . |
| 0 622 049 A1 | 11/1994 | European Pat. Off. . |

Primary Examiner—Michael Buiz
Assistant Examiner—David O. Reip
Attorney, Agent, or Firm—Susan M. Schmitt

[57] ABSTRACT

This invention pertains to a universal hand piece such as a stationary handle or a slap hammer with a universal quick release connector which attaches and detaches to various instruments used in a knee prosthesis implantation surgical procedure. Instrument end pieces to which the hand piece may attach may include, for example, punches, inserters, extractors, impactors, or other instruments in which use of a hand piece is desired.

14 Claims, 6 Drawing Sheets

5,788,701

INSTRUMENT SYSTEM FOR KNEE PROTHESIS IMPLANTATION WITH UNIVERSAL HANDLE OR SLAP HAMMER

This is a continuation of application Ser. No. 08/576,744, filed Dec. 21, 1995 now abandoned.

FIELD OF THE INVENTION

The present invention relates to instruments for implanting an artificial knee, and, in particular, to a universal handle and slap hammer for use with such instruments.

BACKGROUND OF THE INVENTION

During knee replacement surgery a surgeon prepares, among other things, the tibial bone to receive a tibial tray (and insert) and the femoral bone for a femoral implant. A surgeon uses tibial tray trials and femoral trials to determine the tibial and femoral implant sizes, to ensure proper alignment and implant thickness, and to make the appropriate cuts, reams, or recesses in the bones for receipt of the femoral and tibial tray implants. A variety of instruments are used to prepare the bones and to insert and extract the trials and implants. The tibial tray requires tibial bone preparation using punches and or drills. Each type of tibial tray requires different punches and/or drills to prepare the tibial bone for implantation. Standard non-cemented tibial implants require a different opening shape and length than cemented implants. Similarly a modular type implant requires a different bone recess size for both its cemented and non-cemented versions.

Typically, during tibial preparation procedures, a tibial tray trial is selected to correspond with the implant type. Accordingly, the tibial tray trial will have an opening to accommodate the appropriate punch and/or drill shape for that particular implant type. A punch, and, if necessary, a drill is used to form a recess in the tibial bone into which the keel of the tibial implant is to be placed. Typically the punch has a handle with a punching end piece and a guide for receiving the cutting piece, located on the end of the handle. Each type of punch has a different end piece and guide. Thus, for each type of implant, a different handle, end piece, and punch guide is required. Furthermore, a slap hammer may be used instead of a handle, for example, in situations where it may be desirable to extract the punch. Thus, for each type of punch, a different slap hammer would be required.

A handle is typically permanently attached to a tibial tray inserter. A tibial tray inserter is typically attached to a tibial tray to place the tray and be inserted on a prepared tibial bone. The handle on the inserter is used to apply pressure as the tray is being inserted. The tray inserter with its handle is then detached from the tray which is left on the tibial bone.

A handle is typically permanently attached to a tibial tray impactor, a poly tibial component impactor or a femoral impactor. A tibial tray impactor is placed on an inserted tibial tray and is used to hammer the tray further into the prepared bone to ensure a secure fit. Likewise, a poly tibial component impactor is placed on a revision or stabilized tray insert and is used to seat the implant onto the prepared tibial tray. Also, a femoral impactor is placed on an inserted femoral implant component and used to hammer the femoral implant into place.

A slap hammer or handle is attached to a femoral inserter/extractor. A cemented femoral implant or a femoral trial is held by the inserter/extractor and is placed on a prepared femoral bone. The slap hammer or handle is held and used to apply pressure as the implant or trial is being inserted. The slap hammer may also be used to extract the femoral trial component by repeatedly pulling up on the slap hammer.

Presently all punches, inserters, impactors, and extractors of this type are permanently attached to their respective handles or slap hammers, or, as is the case with the punches, they are attached with screws to the handle or slap hammer. Therefore, it is desirable to provide an artificial knee implant instrument system in which less pieces are required and which will save time, money and space in the operating room.

SUMMARY OF THE INVENTION

Accordingly, the present invention includes a universal connect/disconnect mechanism for a universal handle and/or slap hammer. A preferred embodiment includes a quick-release mechanism located at the distal end of the handle or slap hammer. The quick-release mechanism is adapted to attach and detach from modular components of an implant instrument system including punches, inserters, impactors, extractors, etc.

In a preferred embodiment, the universal handle and slap hammer attach firmly to the modular components, with the quick-release mechanism comprising a captive spring loaded sliding pin that locks the handle or slap hammer into position. The sliding pin is attached to a knob which when retracted allows the connecting portion to engage with a mating part of a punch, inserter, impactor, extractor or any similar modular component of the system. A T-shaped slot of the modular component mating portion receives the end of the universal handle or slap hammer. When the knob of the handle or slap hammer is released, the pin extends into the hole in the modular component thereby preventing the end of the universal handle or slap hammer from disengaging from the modular component. The handle or slap hammer is disengaged in a similar manner by retracting the knob, drawing the sliding pin back into the body of the handle/slap hammer and sliding the quick release mechanism out of the T-shaped slot allowing quick attachment and detachment from the mating component. The handle or slap hammer may be connected or disconnected using one hand, leaving the other hand free for other purposes.

DETAILED DESCRIPTION OF THE DRAWINGS

DETAILED DESCRIPTION OF THE INVENTION

Figure 1:
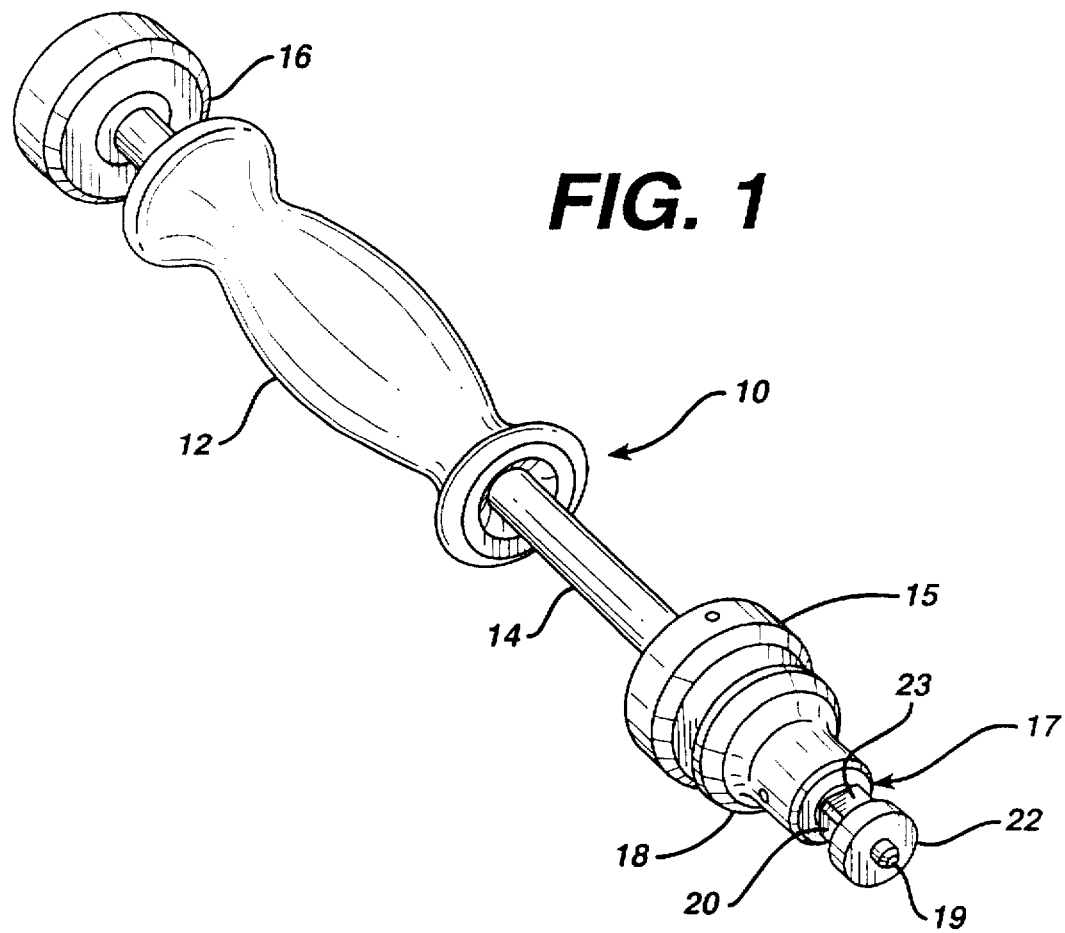
FIG. 1 illustrates a perspective view of a universal slap hammer of the system of the present invention.

Referring now to FIG. 1, there is illustrated a slap hammer 10 with a universal quick connect/disconnect mechanism 17. The slap hammer 10 includes a sliding handle member 12 having an opening 13 through which the stem 14 of the slap hammer extends. The handle member 12 is arranged to slide up and down between stops 15, 16. The slap hammer 10 further comprises quick-release mechanism 17 extending distally from the stem 14. The quick-release mechanism 17 comprises a knob 18, a pin 19, and a universal connecting portion 20 having a T-shaped longitudinal cross-section. The universal connecting portion 20 is coupled to the stem 14, and located at the distal end of the slap hammer 10. The pin 19, coupled to the knob 18, extends distally of knob 18 through the connecting member 20. The knob 18 is spring-loaded in a distal direction and is adapted to move between stop 16 and connecting member 20. When the knob 18 is moved in a proximal direction, the pin 19 is retracted into the connecting member 20. When the knob 18 is released, the spring-loaded bias of the knob 18 causes the knob 18 and pin 19 to move in a distal direction so that the pin 19 extends distally from the connecting member 20.

Figure 2:
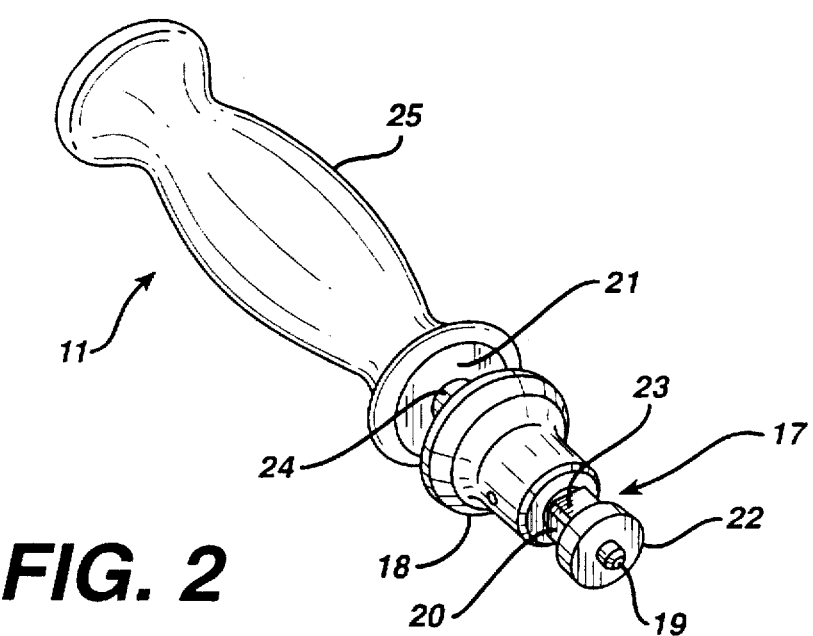
FIG. 2 illustrates a perspective view of a universal handle of the system of the present invention.

Referring now to FIG. 2, a handle 11 comprises a handle portion 25, a stem 24, and a quick release mechanism 17 located at the distal end of the stem 24. The quick release mechanism 17 comprises a knob 18, a pin 19 coupled to the knob 18, and connecting member 20 coupled to the stem 24 through the knob 18. The quick release mechanism is the same device as the quick-release mechanism 17 on the slap hammer 10 of FIG. 1. The knob 18 is spring-loaded in a distal direction and is adapted to move between the distal end 21 of the handle portion 25 and connecting member 20. When the knob 18 is moved in a proximal direction, the pin 19 is retracted into the connecting member 20. When the knob 18 is released, the spring-loaded bias of the knob 18 causes the knob 18 and pin 19 to move in a distal direction so that the pin 19 extends distally from the connecting member 20.

Figure 3:
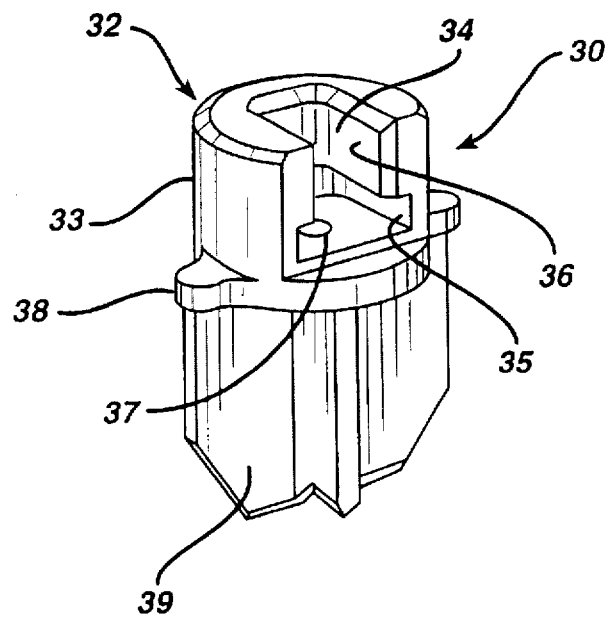
FIG. 3 illustrates a perspective view of a non-cemented standard keel punch of the present invention.
Figure 4:
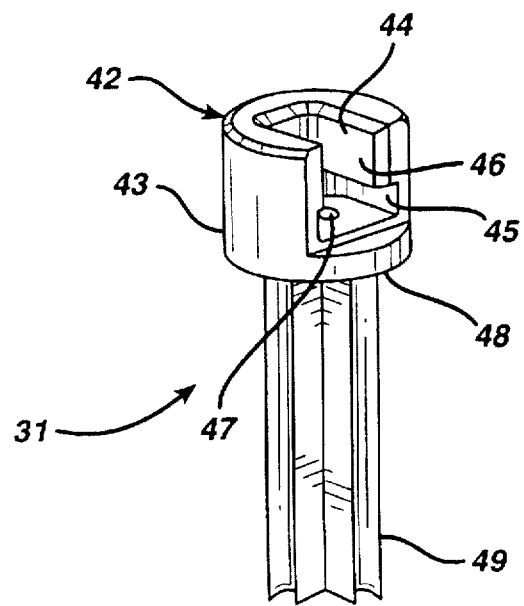
FIG. 4 illustrates a perspective view of a cemented standard keel punch of the present invention.

The connecting member 20, included with both the slap hammer 10 and handle 11, is arranged to couple with the non-cemented standard punch 30 (FIG. 3) and the standard cement punch 31 (FIG. 4). The standard non-cemented punch 30 is used to form a shape in the tibia to receive a standard or cruciform tibial keel. The standard cement punch 31 is arranged to form an extra recess in the tibia to provide additional space around a standard or cruciform keel after the standard non-cemented punch 30 is used to receive a cemented tibial stem.

Referring to FIG. 3, the non-cemented punch 30 comprises a universal connector 32 having a cylindrical member 33 with an opening 34 in its outer circumference for receiving the connecting member 20. The opening 34 includes a groove 35 for receiving a lower portion 22 of the connecting member 20, and a narrower opening 36 for receiving an upper portion 23 of the connecting member 20. The non-cemented punch 30 finally comprises an opening 37 located on the bottom of the groove 35 for receiving the pin 19 of the connecting member 20 to lock the connecting member 20 to the non-cemented punch 30. The connector 32 is coupled to the base 38 of the non-cemented punch 30. The base 38 has an end piece 39 which has appropriate shape for forming the recess the tibial bone to receive a similarly shaped keel of a standard keel implant.

The standard cement punch 31 includes a universal connector 42 comprising a cylindrical member 43 with an opening 44 in its outer circumference. The opening 44 includes a groove 45 for receiving the lower portion 22 of the connecting member 20; narrower opening 46 for receiving the upper portion 23 of the connecting member 20; and an opening 47 for receiving the pin 19. The universal connector 42 operates in a similar manner as the connector 32 of the non-cemented punch 30 as described above. The connector 42 is coupled to the base 40 of the cement punch 31. Cement punch 31 includes an end piece 41 extending distally from the base 40 and having a size and length corresponding to the desired formed recess for a standard keel tibial implant, in a cemented application, i.e., typically longer than the non-cemented punch.

The punch 30 is selected and attached with the connecting portion 20 to either the slap hammer 10 or the handle 11. The punch 30 is inserted through an opening in the punch guide (not shown) and in a tray trial (FIG. 7) to which the punch guide is attached. The user holds the handle 11 and applies pressure to form the recess in the tibia. Alternatively, if the slap hammer 10 is used, the user holds the handle portion 12 and moves it up and down, along the stem 14 to apply pressure, particularly as the handle portion 12 hits the stop 16, to form the recess in the tibia. The slap hammer 10 may then be used to extract the punch 30 or 31 by applying more pressure as the handle portion 12 hits the stop 15. If a cemented implant is to be used, the process is repeated using slap hammer 10 or handle 11, and the cemented punch 31, to form a recess for receiving cement and a cemented keel.

Figure 5:
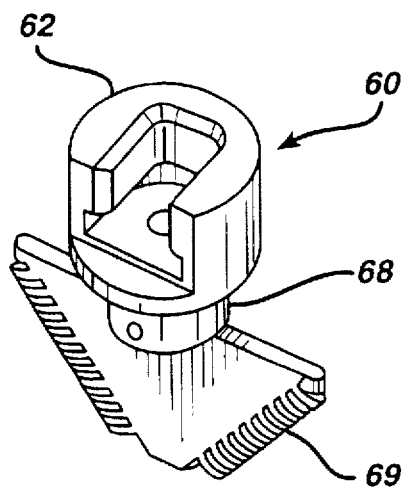
FIG. 5 illustrates a perspective view of a non-cemented modular keel punch of the present invention.
Figure 6:
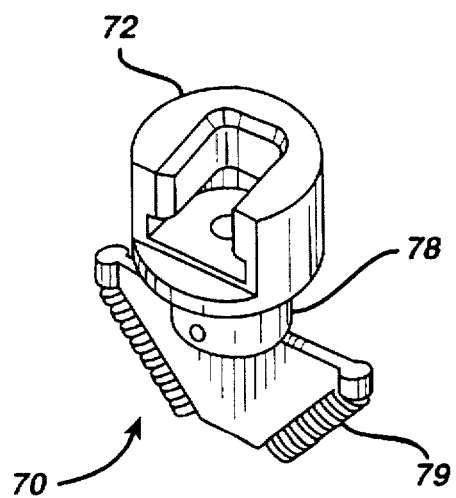
FIG. 6 illustrates a perspective view of a cemented modular keel punch of the present invention.

FIGS. 5 and 6 illustrate a modular press fit tibial keel punches including a modular non-cemented punch 60 (FIG. 5), and a modular cemented punch guide 70 (FIG. 6).

The modular non-cemented punch 60 comprises a universal connector 62, which operates in the same manner as the universal connectors 32 and 42 of FIGS. 3 and 4 to couple the slap hammer 10 or handle 11 to the punch 60. The modular non-cemented punch 60 includes an end piece 69 coupled to a base 68 which is coupled to the universal connector 62. The end piece 69 is used to ream an opening in the tibia.

In use, a punch guide (not shown) is attached to a tray trial (not shown). A drill bushing (not shown) is placed on the opening of the punch guide and a hole of a pre-determined depth is drilled in the tibia. The drill bushing is removed and the punch 60 is attached to the slap hammer 10 or handle 11. The punch 60 is used to further form a shaped tibial bone opening in a manner as described above with respect to the system described with reference to FIG. 4.

In FIG. 6, a modular cemented punch 70 is illustrated comprising a universal connector 72 which operates in the same manner as universal connectors 32, 42 and 62 of FIGS. 3–5 to couple the slap hammer 10 or handle 11 to the punch 70. The modular cemented punch 70 includes an end piece 79 coupled to a base 78 which is coupled to the universal connector 72. The end piece 79 is used to ream an opening in the tibia.

The modular cemented punch 70 is used in the same manner as the modular non-cemented punch 60 in FIG. 5 except that the drill bit and punch 70 are sized and shaped to prepare the tibial bone to accommodate cement and a cemented modular implant.

Figure 7:
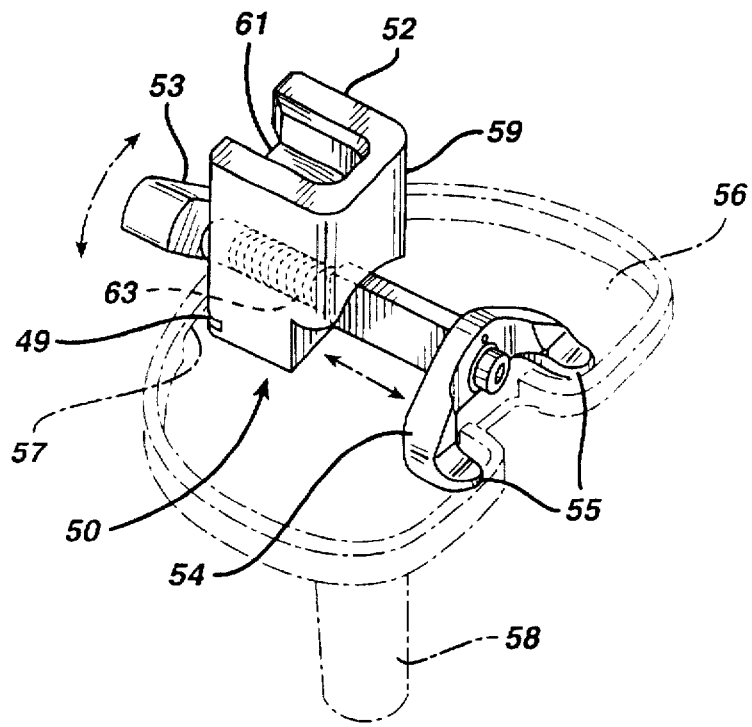
FIG. 7 illustrates a perspective view of a tibial tray inserter of the system of the present invention.

Referring now to FIG. 7, a tibial tray inserter 50 is illustrated comprising: a body 59 with a universal connecting element 52, a tray holder 54 with prongs 55, located is at the posterior end of a rotatable threaded screw 51, and a knob 53 located on the anterior side of the base 59. The knob 53 is coupled to threaded screw 51 which extends through a threaded hole 63 in the body 59. The knob 53 is rotatably coupled to the tray holder 54. The tray holder is extendable from and retractable towards the anterior end of the body 59 by way of rotating knob 53, thereby advancing or retracting the threaded screw 51. The connector 52 includes a lower posterior groove 49 for coupling to the posterior of the rim 57 of a tibial tray 56. The connector 52 further comprises opening 61 including a groove for receiving the lower portion 22 of connecting member 20 and an opening in the bottom of the groove for receiving pin 19 of connecting member 20 to lock the connecting member 20 to the inserter 50. The groove and openings are similar to those of connectors 32, 42 and 62 described above.

In use, the prongs 55 are inserted under the posterior side of the tibial tray rim 57. The connector body 59 is placed on the tray 56 and the knob 53 is rotated in a first direction until the groove 49 of the connector 52 has coupled with the rim 57 on the anterior side of the tray 56. The handle 11 or slap hammer 10 is coupled to the coupling element 52 in a manner as described above with respect to connectors 32, 42, 62 and 72 of FIGS. 3–6. The tray 56 is placed on the tibial bone and pressure is applied to the handle 11 or slap hammer 10 to push the keel 58 of the tray 56 into place. The knob 53 is rotated in the opposite direction to uncouple the inserter 50 from the tray 56 and the inserter 50 is removed.

A variety of inserters and their uses are known in the art. According to the present invention, any such inserter may be used with a similar universal coupling mechanism.

Figure 8:
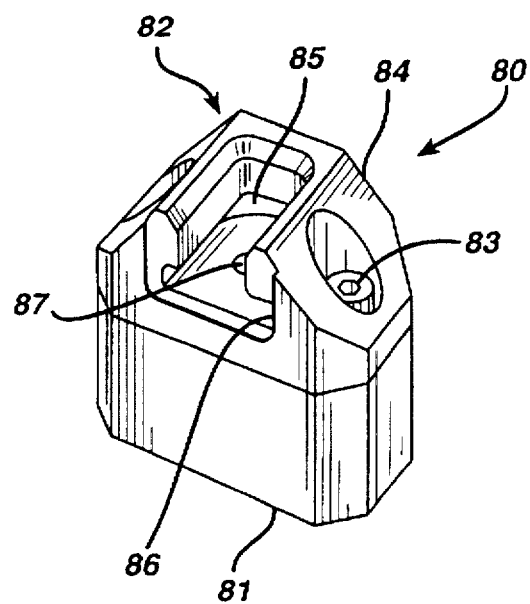
FIG. 8 illustrates a perspective view of a tibial tray impactor of the system of the present invention.

Referring now to FIG. 8, a tibial tray impactor 80 is illustrated comprising a universal connector 82 coupled by way of screws 83 to an impacting block 81. The universal connector 82 comprises a body 84 with an opening 85 in its side. The opening 85 includes a groove 86 for receiving the lower portion 22 of connecting member 20 of handle 11 or slap hammer 10, and an opening 87 in the bottom of the groove 86 for receiving pin 19 of connecting member 20 to lock connecting member 20 to the tibial tray impactor 80.

The universal connector body 84 is made from stainless steel material and the impacting block 81 is made of nylon. The impacting block 81 is shaped to fit within rim 57 of the tray 56.

The impactor 80 is typically used after the tray 56 has been inserted into the prepared tibial cavity. In use the slap hammer 11 or handle 10 is coupled to the universal connector 82 in a manner as described above with respect to connectors 32, 42, 52, 62 and 72. The impacting block 81 is placed at various locations on the tray 56 within the rim 57 to press the tray into position and complete the insertion.

Figure 9:
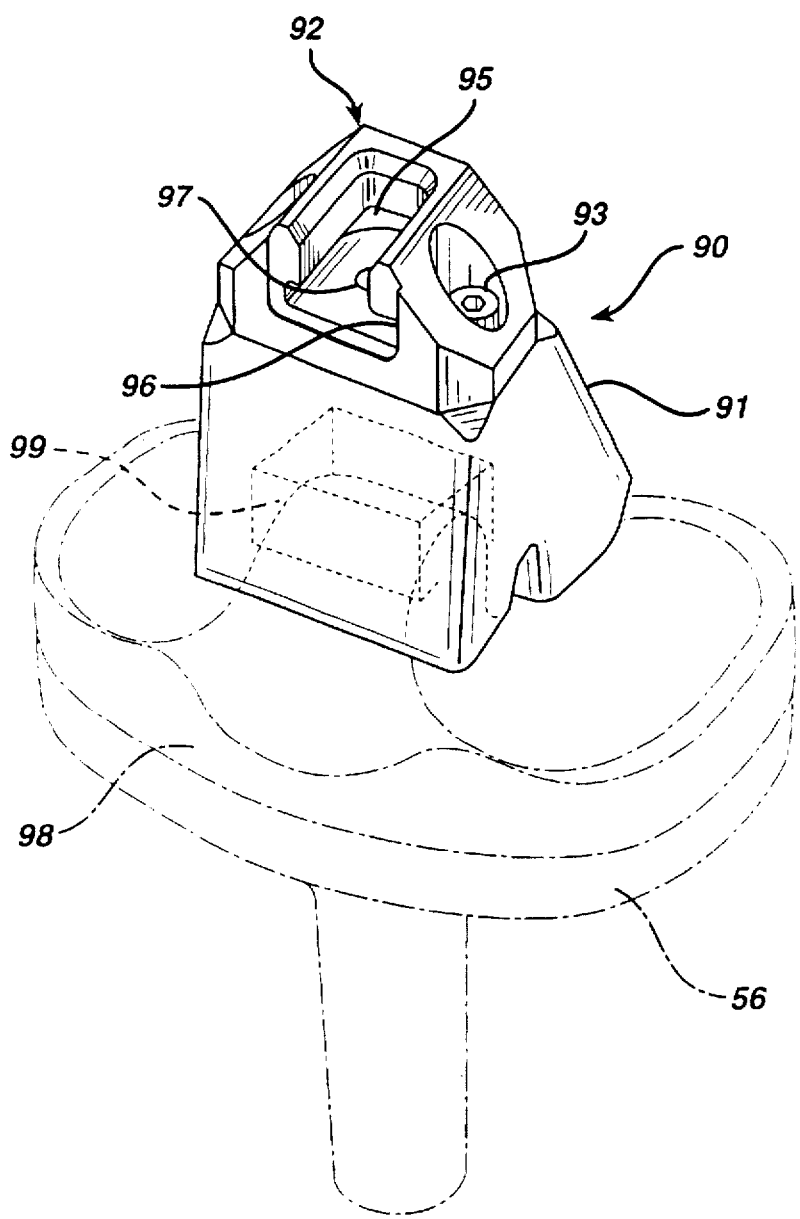
FIG. 9 illustrates a perspective view of a poly tibial component impactor of a system of the invention.

Referring now to FIG. 9, a poly tibial component impactor 90 is illustrated comprising a universal connector 92 coupled by way of screws 93 to an impacting block 91. An indentation 97 is formed in the block 91. The universal connector 92 comprises a body 94 with an opening 95 in its side. The opening 95 includes a groove 96 for receiving the lower portion 22 of connecting member 20 and an opening 97 in the bottom of the groove 96 for receiving pin 19 of connecting member 20 to lock connecting member 20 to the poly tibial component impactor 90.

The universal connector 92 is made from stainless steel and the impacting block 91 is made of nylon. The impacting block 91 is shaped to fit over tibial insert 98 having a spine 99 for stabilization. Such tibial inserts are used, e.g., in revision knees or in stabilized knees. Typically, to implant such a tibial prosthesis, the tibial cavity is purported to receive the keel of a cemented implant. Cement is inserted into the prepared cavity. The steps using the inserter 50 of FIG. 7 and the impactor 80 of FIG. 8 are then repeated.

After the impactor 80 is used the knee is extended to exert force on the tibia until the cement is set. The tibial insert 98 is then placed in the tibial tray 56. The slap hammer 11 or handle 10 is coupled to the universal connector 92 in a manner as described above with respect to connectors 32, 42, 52, 62, 72 and 82. The insert 98 is placed on the tray 56 and the impacting block 91 is placed on the insert 98 with the indentation 97 over the spine 99. Pressure is applied to the handle 11 or slap hammer 10 to complete insertion of the insert 98 into the tray 56.

Figure 10:
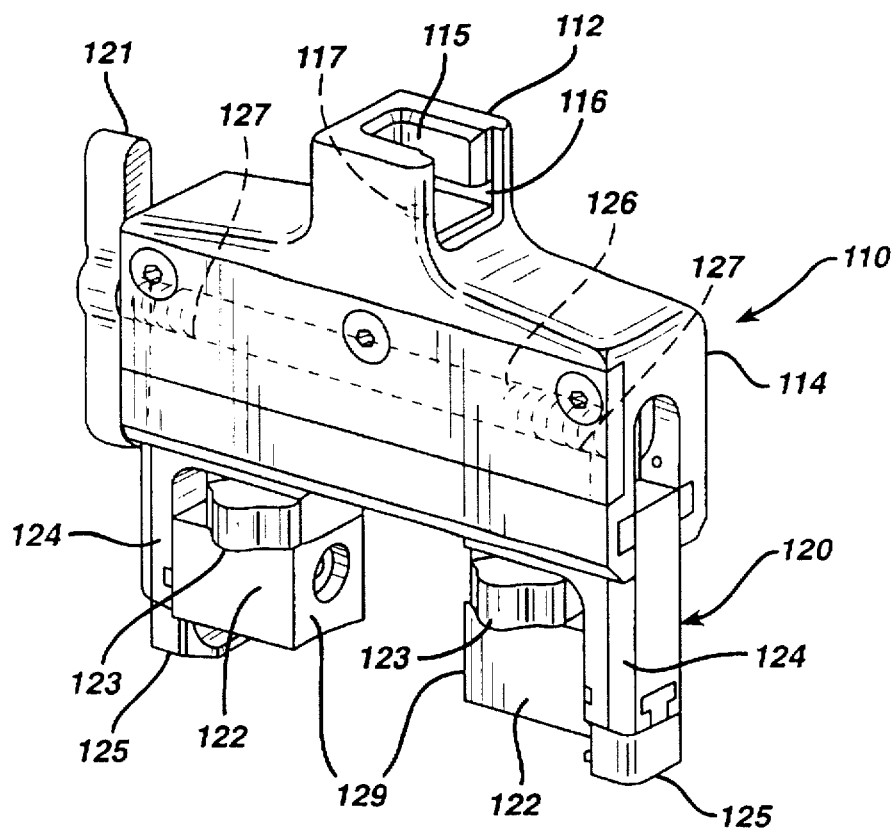
FIG. 10 illustrates a perspective view of femoral inserter/extractor of the system of the present invention.

Referring now to FIG. 10, there is illustrated a femoral inserter/extractor 110 comprising a body 114 having a universal connector 112, moveable grasping device 120, knob 121 for opening and closing the grasping device, nylon holder 122, height adjuster 123, movable bodies 124, and grasping tips 125.

The knob 121 is rotatably coupled to the body 114 with a threaded screw 126 attached to the knob 121. The screw 126 is movably coupled with opposing screw threads 127 of moveable bodies 124. When the screw 126 is rotated by the knob 121, the moveable bodies 124 move towards or away from each other.

The height adjusters 123, nylon holders 122 and grasping tips 125 are mounted on moveable bodies 124. The height adjusters 123 are rotatable 90° to adjust the height or distance from the body 114 to the tips 125. The height adjusters 123 have a variable thickness which changes this height when a 90° rotation is made. The nylon holders 122 include curvatures 127 shaped to fit over the concave curvatures of the top of a femoral implant. The grasping tips 125 extend inwardly from the bodies 124 toward each other.

The universal connector 112 comprises an opening 115 in its side. The opening 115 includes a groove 116 for receiving the lower portion 22 of connecting element 20 on slap hammer 10 or handle 11. The opening 115 further comprises an opening 117 on its bottom for receiving pin 19 of connecting member 20 to lock the connecting member 20 to the femoral inserter/extractor 110.

In use the femoral inserter/extractor is used to grip the femoral trial or femoral implants follows:

The femoral inserter/extractor 15 is coupled to the slap hammer 10 or handle 11 using the connecting member 20 to connect with the universal connector 112 in a similar manner as described above with respect to connectors 32, 42, 52, 62, 72, 82, 92 and 102.

The knob 121 is rotated to move bodies 124 away from each other. The height adjusters 123 are oriented for the femoral height corresponding to the implant size. The condyles of the femoral implant are placed on the holders 122 and the knob is rotated until the tips 125 secure the femoral implant. The implant is then inserted onto the prepared femoral bone.

Figure 11:
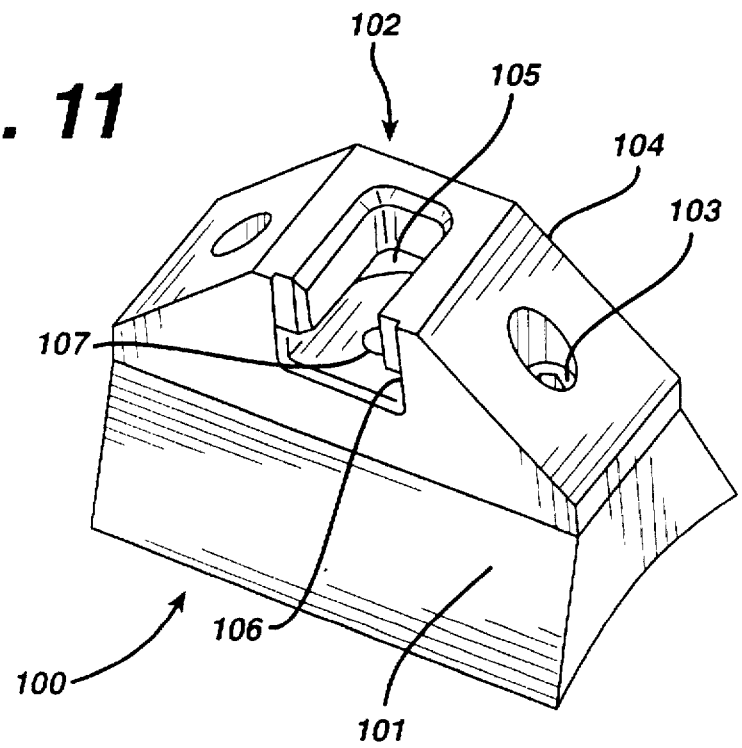
FIG. 11 illustrates a perspective view of a femoral impactor system of the present.

Referring now to FIG. 11, a femoral impactor 100 is illustrated comprising a universal connector 102 coupled by way of screws 103 to impacting block 101. The universal connector 102 comprises a body 104 with an opening 105 in its side. The opening 105 includes a groove 106 for receiving the lower portion 22 of connecting member 20 and an opening 107 in the bottom of the groove 106 for receiving pin 19 of connecting member 20 to lock connecting member 20 to the femoral impactor 100.

The universal connector body 104 is made from stainless steel material and the impacting block 101 is made of nylon.

The impacting block 101 includes indentations 108 shaped to fit over concave surfaces of the femoral condyles.

The impactor 100 is used after the femoral portion has been inserted as illustrated in FIG. 10. The slap hammer 11 or handle 10 is coupled to the universal connector 102 in a manner as described above with respect to connectors 32, 42, 52, 62, 72, 82 and 92. The impactor 100 is typically then used to drive the femoral component into place in the femur by placing the impacting block 101 on the condyle portions of the implant and applying pressure.

Although the present invention is described with respect to particular embodiments and features and uses, numerous variations or equivalents are possible without taking away from the spirit or scope of the claimed invention.

I claim:

1. An artificial knee implantation instrument system comprising:
   an instrument end piece and a universal hand piece adapted to couple and lock with said end piece, wherein said universal handpiece comprises:
   a handle portion; and
   a universal connector coupled to said handle portion, said universal connector comprising:
   a spring-loaded quick release mechanism having a first locked position and a second position; and
   an actuating device adapted to move said release mechanism from said first position to said second position wherein said release mechanism is biased towards said first position; and
   wherein said end piece comprises:
   an instrument portion for performing a step in a prosthetic knee implantation procedure; and
   a connecting portion arranged to receive and lock with said universal connector of said universal hand piece;
   wherein said end piece is selected from a group consisting of: a tibial punch; a tibial tray inserter for placing a tibial tray in a prepared tibial bone; a tibial tray impactor for seating a tibial tray in a prepared tibial bone; a tibial impactor adapted to place a tibial insert in a tibial tray; a femoral inserter for placing a femoral prosthesis in a prepared femoral bone; a femoral impactor for placing a femoral prosthesis onto a prepared femoral bone; and a punch having a Punching end for preparing a tibial bone for a prosthetic implant.

2. The instrument system of claim 1 wherein said handle portion comprises a stationary handle portion fixed to said hand piece.

3. The instrument system of claim 1 wherein said hand piece further comprises a shaft located between a first stop and a second stop, wherein said handle portion comprises a handle slidable over said shaft and between said first and second stops.

4. The instrument of claim 1 wherein said actuating device comprises a slidable knob arranged to move said release mechanism from said first position to said second position.

5. The instrument system of claim 1 wherein said quick-release mechanism comprises a sliding bolt and wherein said connecting portion comprises, a first opening for receiving said universal connector and a second opening for receiving said sliding bolt wherein said sliding bolt extends into said second opening when said universal connector is inserted in said first opening and when said release mechanism is in said first position.

6. The instrument system of claim 5 wherein said connecting portion of said end piece further comprises a locking portion adapted to engage said universal connector of said hand piece in a locked, coupled position with said connecting portion when said sliding bolt is located in said second opening.

7. An artificial knee implantation instrument system comprising:
   a plurality of instrument end pieces and a universal hand piece adapted to couple and lock with each of said plurality of end pieces, wherein said universal handpiece comprises:
   a handle portion; and
   a universal connector coupled to said handle portion, said universal connector comprising:
   a spring-loaded quick release mechanism having a first locked position and a second position; and
   an actuating device adapted to move said release mechanism from said first position to said second position wherein said release mechanism is biased towards said first position; and
   wherein said each of said plurality of end pieces comprises:
   an instrument portion for performing a step in a prosthetic knee implantation procedure; and
   a connecting portion arranged to receive and lock with said universal connector of said universal hand piece;
   wherein each of said plurality of said end pieces is selected from a group consisting of: a tibial punch; a tibial tray inserter for placing a tibial tray in a prepared tibial bone; a tibial tray impactor for seating a tibial tray in a prepared tibial bone; a tibial impactor adapted to place a tibial insert in a tibial tray; a femoral inserter for placing a femoral prosthesis in a prepared femoral bone; a femoral impactor for placing a femoral prosthesis onto a prepared femoral bone; and a punch having a punching end for preparing a tibial bone for a prosthetic implant.

8. An artificial knee implantation instrument system comprising:
   an instrument end piece; and
   a universal hand piece adapted to couple and lock with said end piece, wherein said universal handpiece comprises:
   a handle portion; and
   a universal connector coupled to said handle portion, said universal connector having a T-shaped cross section formed by an upper narrower portion coupled to a lower wider portion and a distal pin, said universal connector further comprising:
   a spring-loaded quick release mechanism having a first locked position wherein said pin extends distally of said lower portion and a second position wherein said pin is retracted towards said lower portion; and
   an actuating device adapted to move said release mechanism from said first position to said second position wherein said release mechanism is biased towards said first position; and
   wherein said end piece comprises:
   an instrument portion for performing a step in a prosthetic knee implantation procedure; and
   a connecting portion arranged to receive and lock with said universal connector of said universal hand piece.

9. The instrument system of claim 8 wherein said connecting portion of said end piece comprises:
   a side wall, a distal end wall and a proximal opening, the side wall including an side opening therethrough for receiving the universal connector, said side opening comprising a wider opening for receiving said lower portion of the universal connector and a narrower opening for receiving said upper portion of the universal connector, said side wall including a groove for receiving said lower portion when said lower portion is inserted through said wider opening; and said distal end wall including a pin opening for receiving the pin of the universal connector when said pin is in said first position to lock the universal connector within the connecting portion.

10. The instrument system of claim 8 wherein said handle portion comprises a stationary handle portion fixed to said hand piece.

11. The instrument system of claim 8 wherein said hand piece further comprises a shaft located between a first stop and a second stop, wherein said handle portion comprises a handle slidable over said shaft and between said first and second stops.

12. The instrument of claim 8 wherein said actuating device comprises a slidable knob arranged to move said release mechanism from said first position to said second position.

13. The instrument system of claim 8 wherein said quick-release mechanism comprises a sliding bolt and wherein said connecting portion comprises, a first opening for receiving said universal connector and a second opening for receiving said sliding bolt wherein said sliding bolt extends into said second opening when said universal connector is inserted in said first opening and when said release mechanism is in said first position.

14. The instrument system of claim 13 wherein said connecting portion of said end piece further comprises a locking portion adapted to engage said universal connector of said hand piece in a locked, coupled position with said connecting portion when said sliding bolt is located in said second opening.

* * * * *